US009220555B2

(12) United States Patent
Asconeguy et al.

(10) Patent No.: US 9,220,555 B2
(45) Date of Patent: Dec. 29, 2015

(54) CRYO-ABLATION DEVICE WITH DEPLOYABLE INJECTION TUBE

(75) Inventors: Alexander J. Asconeguy, Murrieta, CA (US); David Zarbatany, Laguna Niguel, CA (US)

(73) Assignee: Medtronic Ablation Frontiers LLC, Minneapolis, MN (US)

(*) Notice: Subject to any disclaimer, the term of this patent is extended or adjusted under 35 U.S.C. 154(b) by 861 days.

(21) Appl. No.: 12/914,297

(22) Filed: Oct. 28, 2010

(65) Prior Publication Data

US 2012/0109116 A1 May 3, 2012

(51) Int. Cl.
*A61B 18/02* (2006.01)
*A61B 17/00* (2006.01)
*A61B 18/00* (2006.01)
*A61B 18/18* (2006.01)
*A61M 25/10* (2013.01)
*A61M 25/00* (2006.01)
*A61M 25/01* (2006.01)

(52) U.S. Cl.
CPC ....... *A61B 18/02* (2013.01); *A61B 2017/00243* (2013.01); *A61B 2017/00867* (2013.01); *A61B 2018/0022* (2013.01); *A61B 2018/00357* (2013.01); *A61B 2018/0212* (2013.01); *A61B 2018/1861* (2013.01); *A61M 25/104* (2013.01); *A61M 2025/0004* (2013.01); *A61M 2025/0175* (2013.01)

(58) Field of Classification Search
USPC ..................................................... 606/20–26
See application file for complete search history.

(56) References Cited

U.S. PATENT DOCUMENTS

| 4,573,470 | A | * | 3/1986 | Samson et al. ............... 606/194 |
| 4,762,130 | A | * | 8/1988 | Fogarty et al. ............... 606/159 |
| 5,171,233 | A | | 12/1992 | Amplatz et al. |
| 6,149,677 | A | * | 11/2000 | Dobak, III ................... 607/106 |
| 6,264,679 | B1 | * | 7/2001 | Keller et al. ................. 607/105 |
| 6,283,959 | B1 | | 9/2001 | Lalonde et al. |
| 6,575,933 | B1 | * | 6/2003 | Wittenberger et al. .. 604/101.02 |

(Continued)

FOREIGN PATENT DOCUMENTS

| CN | 101868190 B | 12/2012 |
| CN | 101686847 B | 9/2013 |

(Continued)

OTHER PUBLICATIONS

Notice on the First Office Action and Search Report, The State Intellectual Property Office of the People's Republic of China, Nov. 18, 2014, Application/Patent No. 201180050945.9, 8 pages.

*Primary Examiner* — Ronald Hupczey, Jr.
(74) *Attorney, Agent, or Firm* — Christopher & Weisberg, P.A.

(57) ABSTRACT

A medical system is provided, including a catheter body having a proximal portion and a distal portion; a shaft slidably disposed within a portion of the catheter body, the shaft defining a distal tip; a fluid injection tube coupled to the distal portion of the catheter body and the distal tip of the shaft, the fluid injection tube being transitionable from a first geometric configuration to a second geometric configuration; a membrane coupled to the shaft and enclosing at least a portion of the fluid injection tube therein; and a coolant source in fluid communication with the fluid injection tube. The first geometric configuration may be substantially linear, the second geometric configuration may be substantially helical, and the membrane may be tensioned across at least a portion of the fluid injection tube in the second geometric configuration.

18 Claims, 7 Drawing Sheets

(56) References Cited

U.S. PATENT DOCUMENTS

| | | | |
|---|---|---|---|
| 6,579,287 B2 | 6/2003 | Wittenberger et al. | |
| 6,875,209 B2 * | 4/2005 | Zvuloni et al. | 606/21 |
| 6,942,659 B2 | 9/2005 | Lehmann et al. | |
| 7,101,367 B2 * | 9/2006 | Xiao et al. | 606/21 |
| 7,220,257 B1 * | 5/2007 | Lafontaine | 606/21 |
| 7,320,697 B2 | 1/2008 | Demond et al. | |
| 7,500,973 B2 * | 3/2009 | Vancelette et al. | 606/21 |
| 8,298,218 B2 * | 10/2012 | Mahrouche | 606/21 |
| 2001/0037081 A1 * | 11/2001 | Heiner | 604/23 |
| 2003/0208199 A1 * | 11/2003 | Keane | 606/41 |
| 2006/0253114 A1 * | 11/2006 | Saadat | 606/21 |
| 2010/0114269 A1 | 5/2010 | Wittenberger et al. | |
| 2010/0234876 A1 | 9/2010 | Watson | |
| 2011/0009854 A1 * | 1/2011 | Babkin et al. | 606/21 |

FOREIGN PATENT DOCUMENTS

| | | |
|---|---|---|
| WO | 9615825 A1 | 5/1996 |
| WO | 02/07625 A2 | 1/2002 |
| WO | 0207625 A2 | 1/2002 |

* cited by examiner

CRYO-ABLATION DEVICE WITH DEPLOYABLE INJECTION TUBE

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for tissue treatment, and in particular, towards systems and methods of use thereof for thermally ablating cardiac tissue.

BACKGROUND OF THE INVENTION

Minimally invasive devices, such as catheters, are often employed for medical procedures, including those involving mapping, ablation, dilation, and the like. In a particular situation, an ablation procedure may involve creating a series of inter-connecting or otherwise substantially continuous lesions in order to electrically isolate tissue believed to be the source of an arrhythmia. During the course of such a procedure, a physician may employ several different catheters having variations in the geometry and/or dimensions of the ablative element in order to produce the desired ablation pattern and/or continuity. Each catheter may have a unique geometry for creating a specific lesion or pattern, with the multiple catheters being sequentially removed and replaced during a designated procedure to create the desired multiple lesions constituting a pattern or continuous segment of treated tissue. In addition, a selected device may have a substantially fixed geometry or dimension for a specific application and as such, may be limited to use in situations where the fixed dimensions of the device are appropriate. However, variations in the dimensions or characteristics of physiological structures may vary from patient to patient, rendering a device with specific dimensions or fixed configuration ineffective and/or difficult to use. As such, multiple devices having a range of varying fixed dimensions may be needed to successfully perform a desired treatment. Exchanging these various devices during a procedure can cause inaccuracies or movement in the placement and location of the distal tip with respect to the tissue to be ablated, and may further add to the time required to perform the desired treatment. These potential inaccuracies and extended duration of the particular procedure, not to mention the risks of complications from repeatedly inserting and retracting devices to and from an incision site, increase the risk to the patient undergoing treatment.

In addition to the inefficiencies and risks associated with using multiple devices to perform a procedure, the efficacy of certain treatment procedures, such as those involving thermal energy transfer, may be limited by poor thermal conductivity between a device and the tissue site. To provide shorter treatment durations and increased efficacy for the particular treatment provided, it is desirable to optimize the heat transfer between the specific tissue to be treated and the cryogenic element or device. In other words, heat transfer from any tissue other than that selected for treatment, such as blood or other body fluids in or passing through the vicinity of the cryogenic element for example, should be minimized or avoided. Such thermal exchange with tissues or fluids other than that targeted for treatment can reduce the thermal exchange with the targeted tissue and also require additional "cooling power" or refrigerant flow in the case of cryogenic cooling in order to complete the desired treatment. Accordingly, heat transfer with any thermal load other than the tissue to be treated should be reduced or prevented.

Accordingly, in light of the above limitations, it would be desirable to provide a medical device in which the particular size, shape, and/or dimensions of the device may be controlled and modified during use to provide ablative patterns or treatment delivery characteristics of various shapes and continuity, without the need for additional catheters or the like having a single geometric orientation that is limited in its ability to provide multiple ablative patterns or treatment characteristics for a specific tissue region. It would also be desirable to provide an apparatus and methods of use thereof having increased heat transfer efficiency during thermal exchange procedures.

SUMMARY OF THE INVENTION

The present invention advantageously provides apparatus and methods of use thereof in which the particular size, shape, and/or dimensions of the apparatus may be controlled and modified during use to provide ablative patterns or treatment delivery characteristics of various shapes and continuity, as well as having increased heat transfer efficiency during thermal exchange procedures. In particular, a medical device is provided, including an elongate body having a proximal portion and a distal portion; a fluid injection tube coupled to the distal portion of the elongate body; and a pliable element encompassing the fluid injection tube, the injection tube deployable from a substantially linear configuration to an expanded radial configuration. The fluid injection tube defines a plurality of apertures to dispense a fluid into an interior of the pliable element, and a cryogenic coolant source may be in fluid communication with the fluid injection tube. The device may include a shaft slidably disposed within a portion of the elongate body, wherein the fluid injection tube is coupled to the shaft, where the shaft defines a lumen therein for passage of a guide wire, where the shaft is rotatable with respect to the elongate body, and where rotation of the shaft at least partially deploys the fluid injection tube from the substantially linear configuration to the expanded radial configuration. The fluid injection tube may be constructed from a shape memory material, the elongate body may define an exhaust lumen in fluid communication with an interior of the pliable element, and deploying the fluid injection tube into the expanded radial configuration may deform the pliable element to an expanded configuration.

A medical system is also provided, including a catheter body having a proximal portion and a distal portion; a shaft slidably disposed within a portion of the catheter body, the shaft defining a distal tip; a fluid injection tube coupled to the distal portion of the catheter body and the distal tip of the shaft, the fluid injection tube being transitionable from a first geometric configuration to a second geometric configuration; a membrane coupled to the shaft and enclosing at least a portion of the fluid injection tube therein; and a coolant source in fluid communication with the fluid injection tube. The first geometric configuration may be substantially linear and the second geometric configuration may be substantially helical, where the membrane is tensioned across at least a portion of the fluid injection tube in the second geometric configuration and manipulation of the shaft transitions the fluid injection tube from the first geometric configuration to the second geometric configuration.

A method of thermally treating tissue is also provided, including positioning a deformable membrane adjacent to the tissue; transitioning a fluid injection tube within the deformable membrane from a first geometric configuration to a second configuration to expand the deformable membrane; dispersing a coolant through the fluid injection tube into an interior cavity defined by the deformable membrane; and thermally treating the tissue with the deformable membrane. Thermally treating the tissue may include ablating at least a portion of the tissue and the tissue may include cardiac tissue, such as an ostium of a pulmonary vein. The method may include terminating coolant dispersion into the interior cavity; transitioning the fluid injection tube from the second geometric configuration to the first configuration; and removing the deformable membrane from the tissue.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
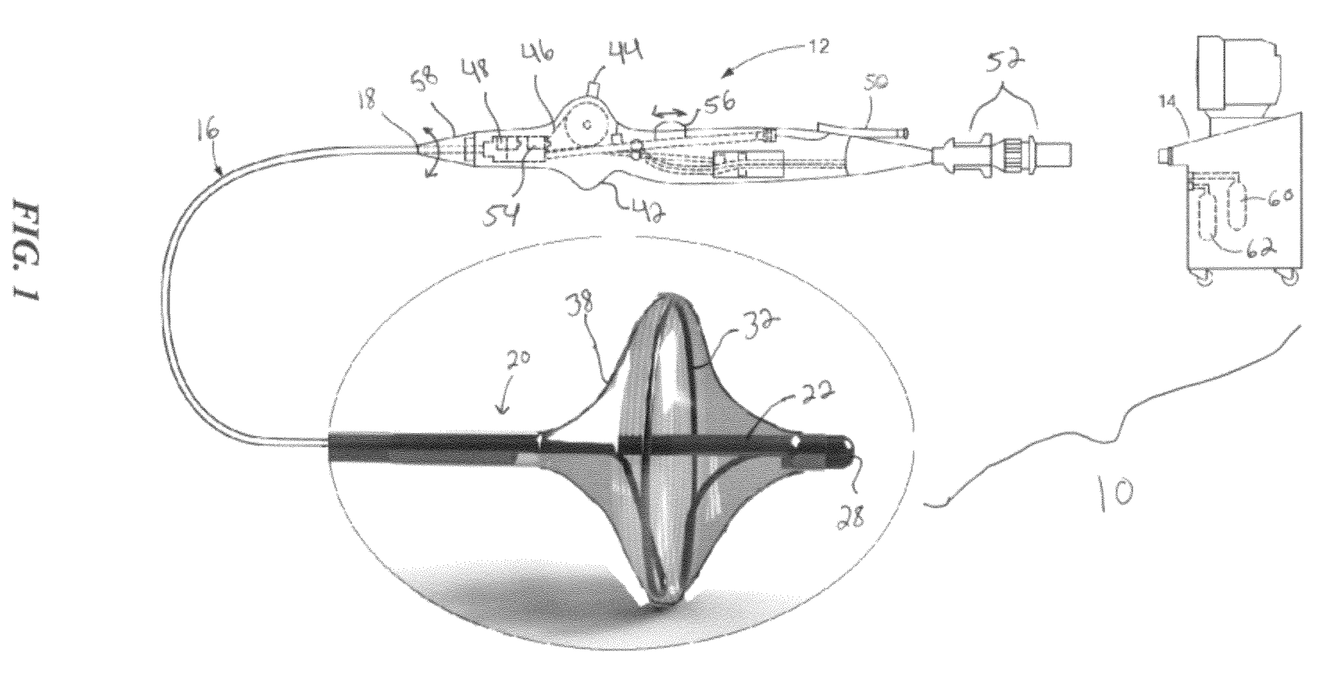
FIG. 1 is an illustration of an embodiment of a medical system constructed in accordance with the principles of the present invention.

The present invention advantageously provides a medical system and methods of use thereof in which the particular size, shape, and/or dimensions of the components of the system may be controlled and modified during use to provide ablative patterns or treatment delivery characteristics of various shapes and continuity, as well as having increased heat transfer efficiency during thermal exchange procedures. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console. The medical device 12 may generally include one or more treatment regions for energetic or other therapeutic interaction between the medical device 12 and a treatment site. The treatment region(s) may deliver, for example, radiofrequency energy, cryogenic therapy, or the like to a tissue area in proximity to the treatment region(s), including cardiac tissue.

Now referring to FIGS. 1-5, the medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16, as discussed in more detail below.

The medical device 12 may include a shaft 22 at least partially disposed within a portion of the elongate body 16. The shaft 22 may extend or otherwise protrude from a distal end of the elongate body 16, and may be movable with respect to the elongate body 16 in longitudinal and rotational directions. That is, the shaft 22 may be slidably and/or rotatably moveable with respect to the elongate body 16. The shaft 22 may further define a lumen 24 therein for the introduction and passage of a guide wire 26. The shaft 22 may include or otherwise be coupled to a distal tip 28 that defines an opening and passage therethrough 30 for the guide wire.

Figure 3:
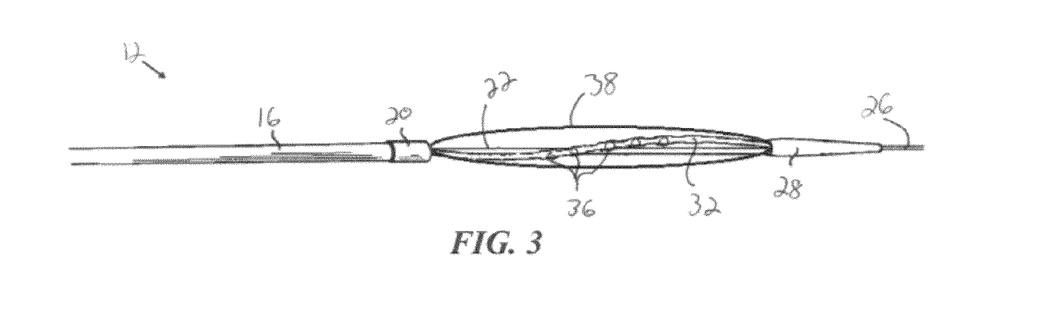
FIG. 3 is an illustration of a geometric configuration of the medical device of FIGS. 1 and 2.
Figure 4:
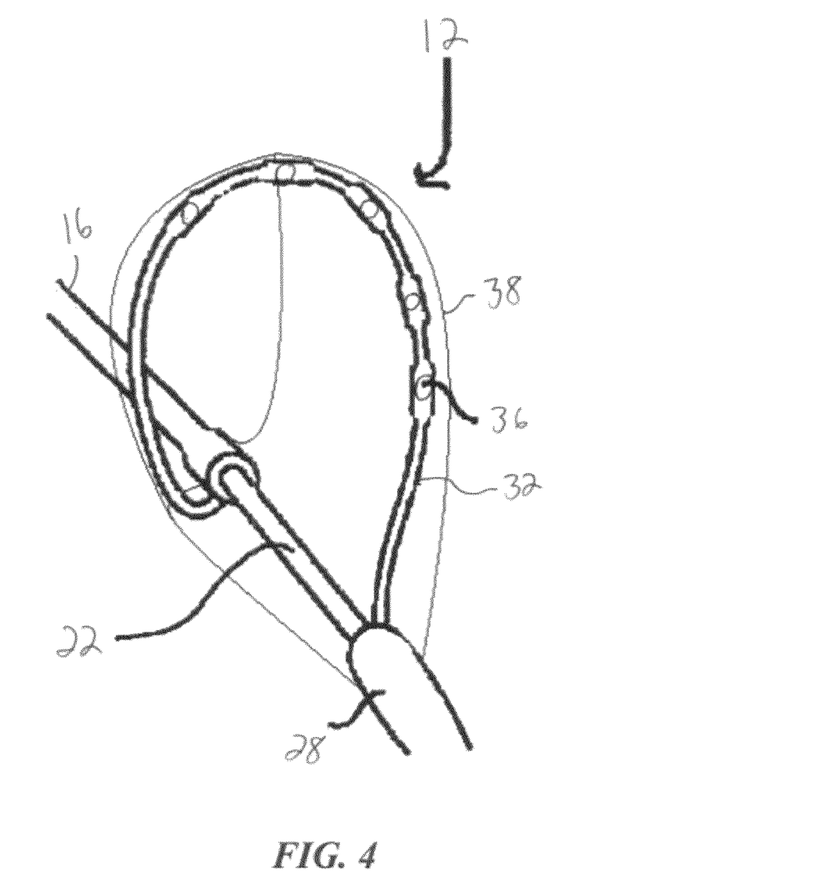
FIG. 4 is an illustration of another geometric configuration of the medical device of FIGS. 1 and 2.
Figure 5:
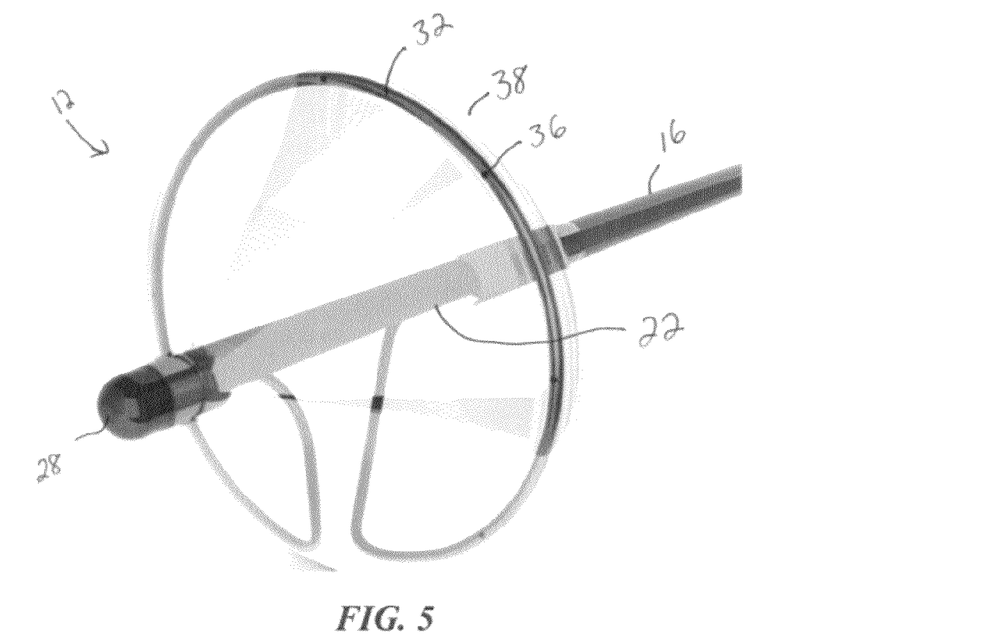
FIG. 5 is an illustration of still another geometric configuration of the medical device of FIGS. 1 and 2.

The medical device 12 may further include a fluid delivery tube 32 at the distal portion. The delivery tube 32 may be coupled to or otherwise extend from the elongate body 16, and may further be coupled to the shaft 22 and/or distal tip of the medical device 12. The fluid delivery tube 32 may define a lumen 34 therein for the passage or delivery of a fluid from the proximal portion of the elongate body 16 and/or the control unit 14 to the distal portion and/or treatment region of the medical device 12. The fluid delivery tube 32 may further include one or more apertures or openings 36 therein to provide for the dispersion or directed ejection of fluid from the lumen to an environment exterior to the fluid delivery tube 32. The fluid delivery tube 32 may be flexible, constructed from a shape memory material (such as Nitinol), and/or include other controllably deformable materials that allow the fluid delivery tube 32 to be manipulated into a plurality of different geometric configurations, shapes, and/or dimensions. For example, the fluid delivery tube 32 may be oriented or deployed into a substantially linear configuration, as shown in FIG. 3, a partial looped or circular configuration, as shown in FIG. 4, and/or a substantially helical configuration, as shown in FIG. 5 and as discussed in more detail below.

Figure 2:
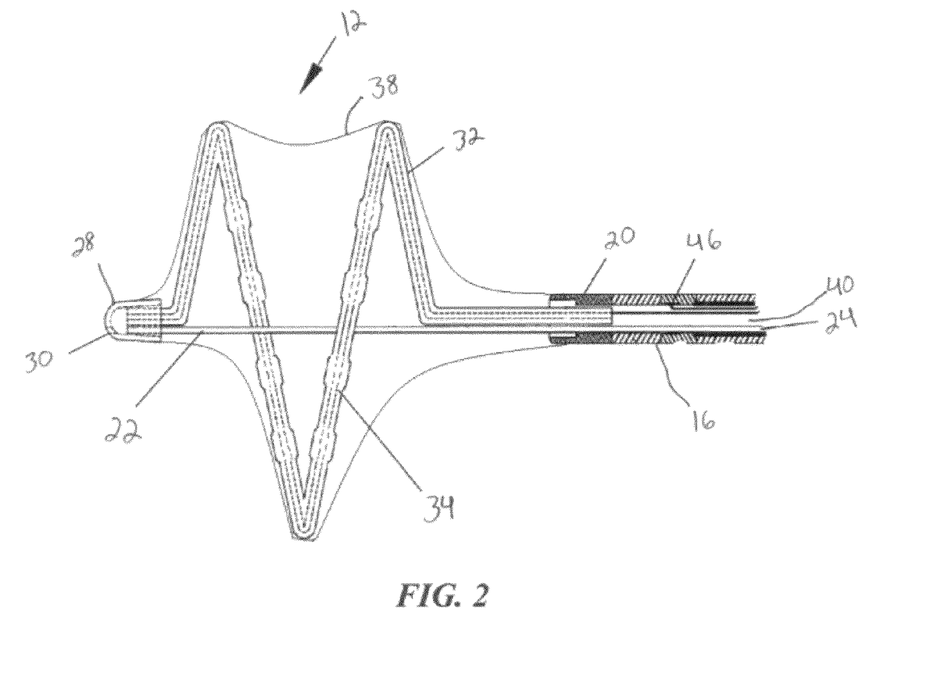
FIG. 2 is a cross-sectional illustration of a medical device of the system in FIG. 1.

The medical device 12 may further include a pliable, deformable element or membrane 38 at the distal portion of the elongate body 16. The membrane 38 may be coupled to a portion of the elongate body 16 and also coupled to a portion of the shaft 22 and/or distal tip to substantially surround or otherwise enclose the fluid delivery tube 32. The membrane 38 defines an interior chamber or region that contains coolant or fluid dispersed from the fluid delivery tube 32, and may be in fluid communication with an exhaust lumen 40 defined by or included in the elongate body 16 for the removal of dispersed coolant from the interior of the membrane 38. The membrane 38 may be tensioned around or closely fit the fluid delivery tube 32, while remaining deformable and pliable into any of a myriad of shapes. The membrane 38 may further include one or more material layers providing for puncture resistance, radiopacity, or the like.

In addition, a mesh (not shown) may be disposed within a portion of the membrane 38 to aid in thermally contacting a targeted tissue region, where the mesh may be cooled by fluid dispersed from the fluid delivery tube 32. Alternatively, the mesh may be positioned on an exterior surface of the membrane to provide structural reinforcement for the membrane 38, as well as providing a thermally conductive segment of the medical device in addition to the fluid delivery tube 32. The mesh may be constructed of a thermally conductive metal or other material providing the desired thermal characteristics and allowing for thermal treatment of an expanded region of contacted tissue.

Figure 6:
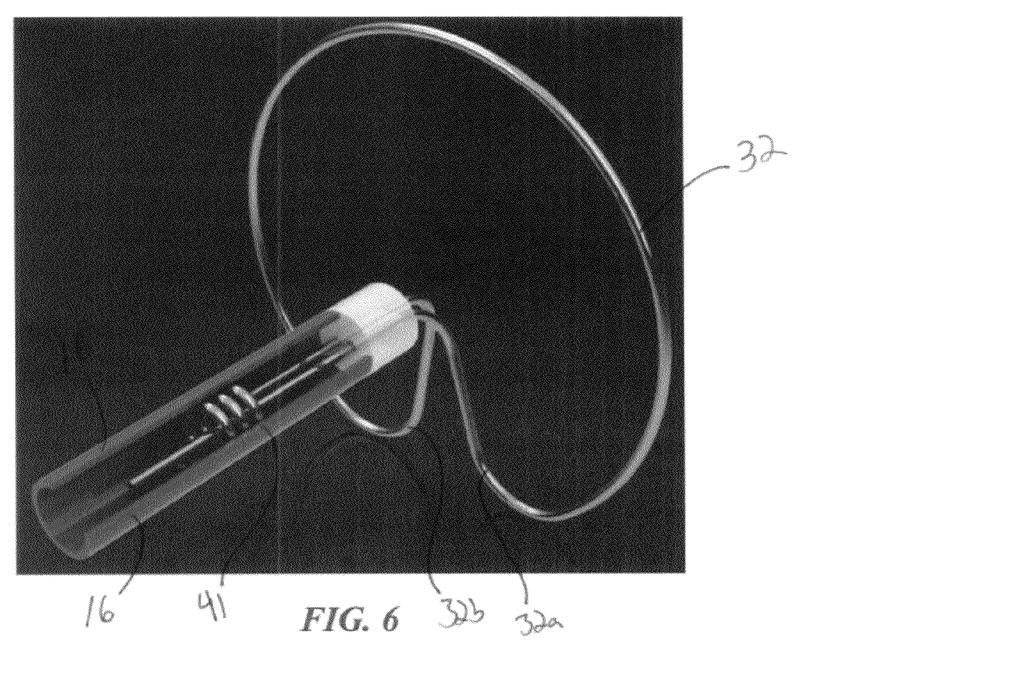
FIG. 6 is an illustration of an embodiment of a medical device constructed in accordance with the principles of the present invention.

Now referring to FIG. 6, the distal portion 20 of the medical device 12 is shown with a portion of the fluid delivery tube 32 coiled about itself at a region proximal of the geometrically configurable portion of the fluid delivery tube 32. Of note, the membrane 40 and other features of the medical device 12 have been omitted from FIG. 6 for illustration purposes only. The coiled portion 41 provides thermal exchange between a delivery portion 32a of the fluid delivery tube 32 directing fluid towards the distal portion of the medical device 12 and a fluid return portion 32b of the fluid delivery tube 32 that moves fluid away from the distal portion of the medical device 12. In a particular example, the fluid delivery conduit may contain a flowing coolant within its interior rather than dispersing a fluid or coolant outward and into an interior of the membrane 38. The temperature of the coolant or fluid flowing within the fluid delivery conduit 32 may be reduced through one or more Joule-Thompson expansions within the fluid delivery conduit 32 itself, e.g., one or more nozzles (not shown) or fluid expansion elements may be disposed within the fluid delivery conduit 32 to effect a phase change and/or temperature reduction of the fluid. Accordingly, the temperature of fluid in the return portion 32b of the fluid delivery conduit 32 may be less than the temperature of the fluid in the delivery portion 32a, and the coiled portion 41 may thus act as a heat exchanger to subcool the delivery portion 32a. The coiled portion 41 may be contained within a portion of the elongate body 16, and may be movable and/or slidable with respect to the shaft, other portions of the fluid delivery tube 32, or the like as described further herein.

Figure 7:
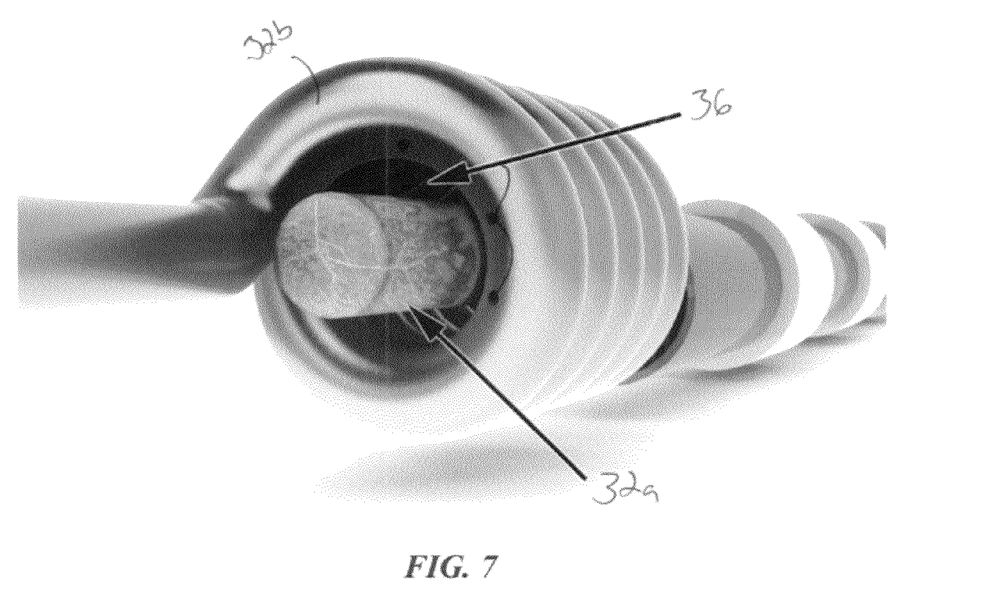
FIG. 7 is another illustration of an embodiment of a medical device constructed in accordance with the principles of the present invention.

Now turning to FIG. 7, an additional view of the coiled portion 41 is shown looking distally. The coiled portion 41 and/or the return segment 32b of the fluid delivery tube 32 may include one or more apertures that disperse coolant or a fluid onto the delivery portion 32a of the fluid delivery tube 32. The dispersed coolant reduces the temperature of the delivery portion 32a, thus allowing it to be used to thermally treat a targeted tissue region. Moreover, the fluid dispersion may be limited to a sealed portion of the elongate body 16, thereby reducing the likelihood of a leak or egress of fluid into the surrounding tissue.

Referring again to FIG. 1, the medical device 12 may include a handle 42 coupled to the proximal portion of the elongate body 16, where the handle 42 may include one or more components such as a lever or knob 44 for manipulating the catheter body and/or additional components of the medical device 12 14. For example, a pull wire 46 with a proximal end and a distal end may have its distal end anchored to the elongate body 16 at or near the distal end. The proximal end of the pull wire may be anchored to an element such as a cam in communication with and responsive to the lever 44.

The handle 42 can further include circuitry for identification and/or use in controlling of the medical device 12 or another component of the system. For example, the handle 42 may include one or more pressure sensors 48 to monitor the fluid pressure within the medical device 12. Additionally, the handle 42 may be provided with a fitting 50 for receiving a guide wire that may be passed into the guide wire lumen. The handle 42 may also include connectors 52 that are matable directly to a fluid supply/exhaust and control unit 14 or indirectly by way of one or more umbilicals. The handle 42 may further include blood detection circuitry in fluid and/or optical communication with the injection, exhaust and/or interstitial lumens. The handle 42 may also include a pressure relief valve 54 in fluid communication with the fluid delivery tube 32 and/or exhaust lumens to automatically open under a predetermined threshold value in the event that value is exceeded.

Continuing to refer to FIG. 1, the medical device 12 may include an actuator element 56 that is movably coupled to the proximal portion of the elongate body 16 and/or the handle 42. The actuator element 56 may further be coupled to a proximal portion of the shaft 22 such that manipulating the actuator element 56 in a longitudinal direction causes the shaft 22 to slide towards either of the proximal or distal portions of the elongate body 16. The actuator element 56 may include a thumb-slide, a push-button, a rotating lever, or other mechanical structure for providing a movable coupling to the elongate body 16, the handle 42, and/or the shaft 22. Moreover, the actuator element 56 may be movably coupled to the handle 42 such that the actuator element is movable into individual, distinct positions, and is able to be releasably secured in any one of the distinct positions.

The medical device 12 may include a rotational control element 58 that is rotatably coupled to the proximal portion of the elongate body 16 and/or the handle 42. The rotational control element 58 may further be coupled to a proximal portion of the shaft 22 such that rotating the rotational control element 58 about a longitudinal axis of the handle 42 and/or elongate body 16 results in similar rotation of the shaft 22 at the distal portion of the medical device 12. The rotational control element 58 may include a knob, dial, or other mechanical structure for providing a rotatable coupling to the elongate body 16, the handle 42, and/or the shaft 22. Moreover, the rotational control element 58 may be rotatably coupled to the handle 42 and/or elongate body 16 such that the rotational control element is movable into individual, distinct positions, and is able to be releasably secured in any one of the distinct positions.

The fluid delivery tube 32 and the membrane 38 are coupled to the shaft 22, and as such, movement of the shaft 22 allows the controllable transition of the fluid delivery tube 32 and the membrane 38 from one geometric shape, configuration, or dimension to another. By sliding and rotating the shaft 22, through manipulation of the actuator element 56 and the rotational control element 58 of the handle 42 for example, the fluid delivery tube 32 can be manipulated into various geometries for the desired clinical or therapeutic effect. For example, the shaft 22 can be retracted in a proximal direction with respect to the elongate body 16 to transition the fluid delivery tube 32 from a near linear configuration (FIG. 3) to a partial circumferential, looped configuration (i.e., a partial helical or spiral shape, as shown in FIG. 4). The orientation of the looped configuration can further be modified by rotating the shaft 22 through manipulation of the rotational control element.

By using both rotational and longitudinal manipulation of the shaft 22, the dimensions and geometry of the fluid delivery tube 32, and thus the surrounding membrane 38, can be increased and decreased as desired. For example, the fluid delivery tube 32 may be manipulated through a range of diameters from about approximately 15 mm to a approximately 35 mm to accommodate varied anatomical contours or structures, such as those neighboring pulmonary vein ostia (including non-circular ostia), for example. On the other hand, manipulation of the control shaft 22 can attain a near-linear configuration of the fluid delivery tube 32 to treat or deliver thermal energy along a linear segment of tissue. The linear configuration also facilitates ease of introduction and removal of the medical device 12 through the vasculature (which may be further aided by the deflective, steering mechanisms described above).

The system may further include one or more sensors to monitor the operating parameters throughout the system, including for example, pressure, temperature, flow rates, volume, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

In an exemplary system, a fluid supply 60 including a coolant, cryogenic refrigerant, or the like, an exhaust or scavenging system (not shown) for recovering or venting expended fluid for re-use or disposal, as well as various control mechanisms for the medical system may be housed in the console. In addition to providing an exhaust function for the catheter fluid supply, the console may also include pumps, valves, controllers or the like to recover and/or re-circulate fluid delivered to the handle 42, the elongate body 16, and/or the fluid pathways of the medical device 12. A vacuum pump 62 in the control unit 14 may create a low-pressure environment in one or more conduits within the medical device 12 so that fluid is drawn into the conduit(s)/lumen(s) of the elongate body 16, away from the distal portion and towards the proximal portion of the elongate body 16. The control unit 14 may include one or more controllers, processors, and/or software modules containing instructions or algorithms to provide for the automated operation and performance of the features, sequences, or procedures described herein.

While the medical device 12 may be in fluid communication with a cryogenic fluid source to cryogenically treat selected tissue, it is also contemplated that the medical device 12 may alternatively or additionally include one or more electrically conductive portions or electrodes thereon coupled to a radiofrequency generator or power source as a treatment or diagnostic mechanism.

Figure 8:
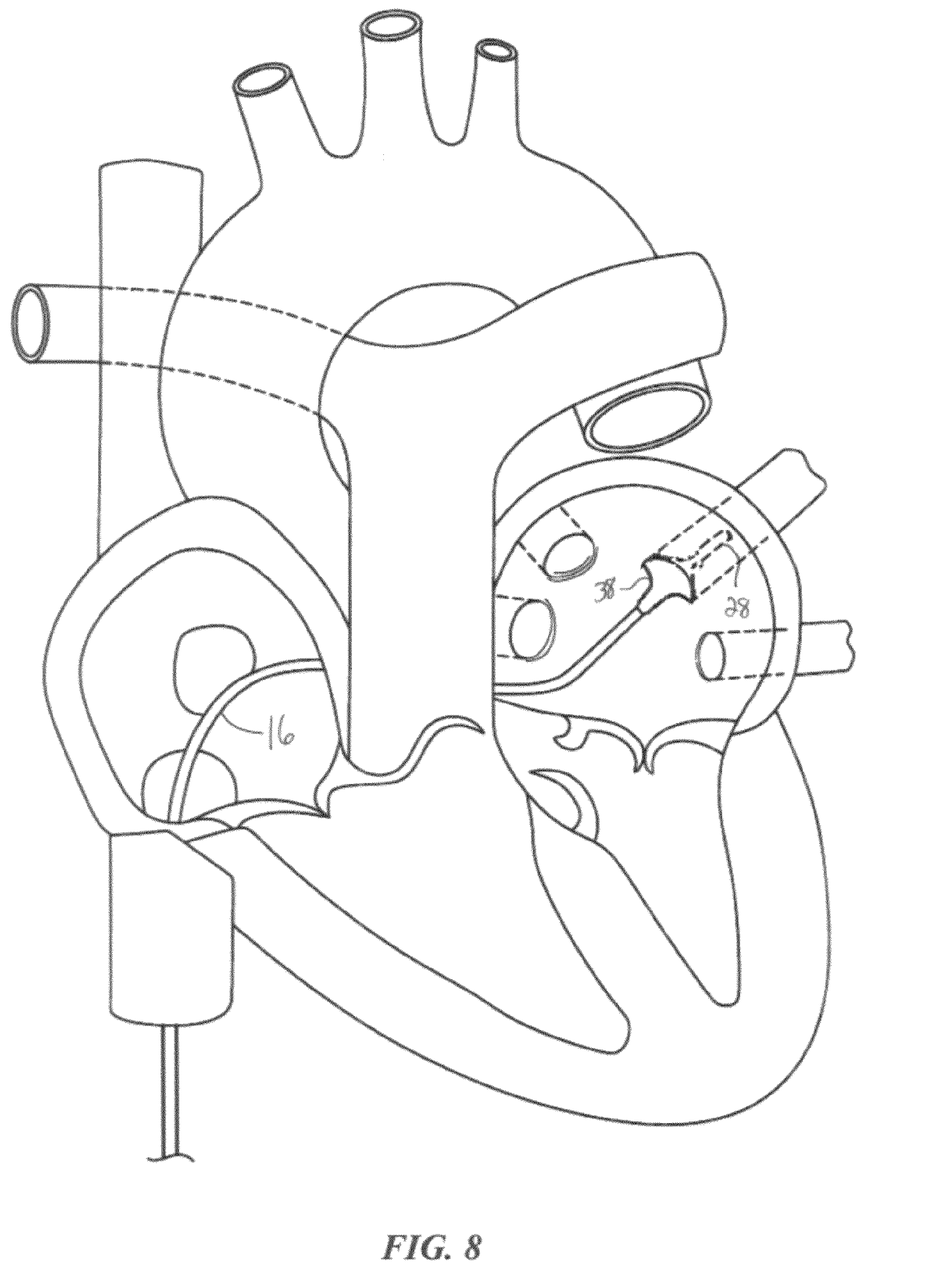
FIG. 8 is an illustration of an exemplary use of an embodiment of a medical system in accordance with the principles of the present invention.
Figure 9:
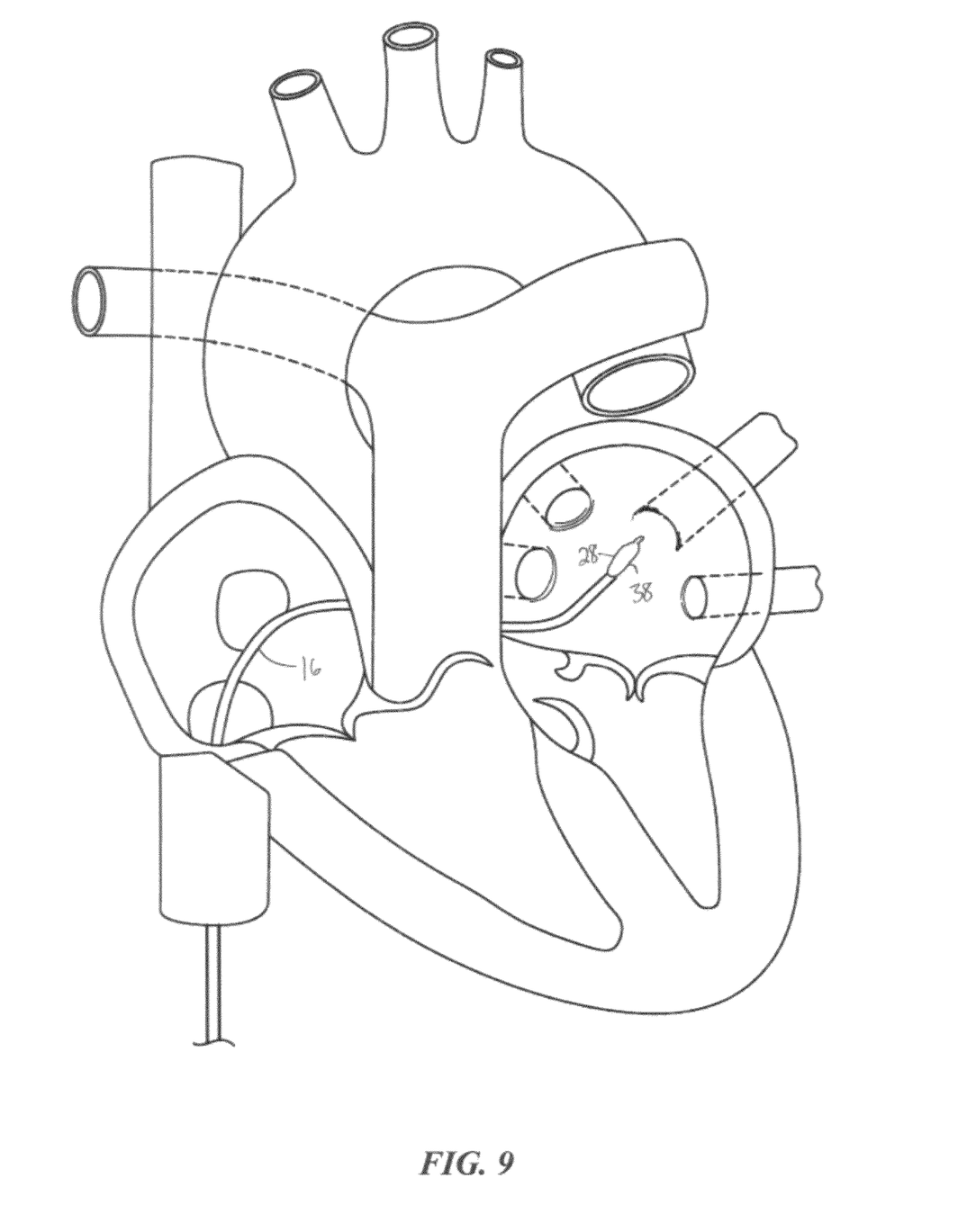
FIG. 9 is another illustration of an exemplary use of an embodiment of a medical system in accordance with the principles of the present invention.

Now referring to FIGS. 8-9, in an exemplary method of use, the medical system may be used to deliver therapeutic treatment to a targeted tissue area. For example, the medical device 12 may be positioned and operated to thermally treat or ablate a targeted tissue region in the heart, such as a pulmonary vein opening or ostia. Using the actuator element 56 and/or rotational control element 58 to adjust the shaft 22, the fluid delivery tube 32 may be manipulated into a deployed, circumferential or substantially helical configuration (such as that shown in FIGS. 4-5 for example). Deploying or manipulating the fluid delivery tube 32 also results in a deformation in the conformable membrane 38 surrounding the fluid delivery tube 32. Once the desired geometric configuration has been attained, the membrane 38 (and the fluid delivery tube 32 underneath it), may be placed adjacent to and/or in contact with a targeted tissue area. Once the distal portion has been positioned where desired, it may be operated to thermally treat the tissue. For example, a cryogenic coolant or fluid may be circulated through the fluid delivery tube 32 and into the interior of the membrane 38, thereby reducing the temperature of the membrane 38 and the tissue in proximity to it. The extent of the thermal exchange and/or realized temperatures of the membrane 38 and thus the tissue may be manipulated by one or more controls in the control unit 14 to provide for tissue ablation, mapping, or other therapeutic and/or diagnostic function.

Of note, as the apertures 36 of the fluid delivery tube 32 are immediately adjacent an interior surface of the membrane 38, which may be in contact with the targeted tissue site on the opposite side of the membrane 38, there is a substantially reduced, if not altogether eliminated, extraneous thermal load or environment to interfere with the thermal exchange between the fluid delivery tube 32, the membrane 38, and the adjacent tissue. In other words, the close proximity of the coolant dispersion from the fluid delivery tube 32 towards the membrane 38 combined with the close proximity of the tissue to the membrane 38 reduces the likelihood of any significant heat loss from fluid flow around other portions of the exterior of the medical device 12.

Upon achieving the desired effect with the distal portion of the medical device 12 in the first geometric configuration, the flow of coolant to the fluid delivery tube 32 and thus the interior of the membrane 38 may be discontinued. The distal portion of the medical device 12 may then be repositioned or configured into a second geometric configuration (such as that shown in FIG. 3, for example) in proximity to a tissue region where additional thermal treatment may be performed. The transition may be achieved by manipulating the actuator element 56 and/or the rotational control element 58 as described above. Once the desired geometric configuration has been achieved, coolant may be re-introduced or otherwise circulated through the fluid delivery tube 32 and into the interior of the membrane 38. Accordingly, the second geometric configuration may be used to impart a second tissue lesion and/or thermally affected area having a varied geometric pattern and/or dimension to that of the first tissue lesion. The manipulation and/or repositioning of the distal portion of the medical device 12 may be repeated as needed to achieve the desired therapeutic effect.

The controllable geometric configuration of the distal portion of the medical device generally provides the ability to deliver therapeutic treatment in a variety of different geometric configurations, dimensions or shapes with a single device and further provides an ability to ensure continuity of an ablation lesion or pattern with a single device, rather than with several different devices. In addition, varying range of shapes and dimensions attainable with the manipulable fluid delivery tube provides varying degrees of precision in treating tissue and/or creating an ablative lesion as a result of its respective geometric configurations, shapes, and/or dimensions. For example, the a deployed, helical or circumferential configuration may be used during an initial stage of a procedure to treat a relatively large area of tissue, while a second linear or otherwise decreased profile may subsequently be used to treat smaller sections or specific areas of tissues within the broad region that require additional therapy. Although the exemplary use described above employed first and second geometric configurations, it is contemplated that a shaping element capable of more than two configurations may be employed and achieved through a combination of mechanical, thermal, and/or electrical forces, as well as through characteristics provided through material selection in the construction of the shaping element. Moreover, while examples and illustrations of particular geometric configurations have been provided, it is understood that virtually any shapes, configurations, and/or dimensions may be included and/or achieved by the medical device of the present invention, including but not limited to those shapes illustrated and described herein. A particular geometric configuration may include circular, conical, concave, convex, rounded, or flattened features and/or combinations thereof. Accordingly, an embodiment of the medical device of the present invention may be able to provide focal lesions, circular lesions, linear lesions, circumferential lesions, and combinations thereof.

It will be appreciated by persons skilled in the art that the present invention is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention. A variety of modifications and variations are possible in light of the above teachings without departing from the scope and spirit of the invention, which is limited only by the following claims.

What is claimed is:

1. A medical device, comprising:
  an elongate body having a proximal portion and a distal portion;
  a linear shaft coaxial with and extending from the distal portion of the elongate body, the linear shaft having a proximal portion and a distal portion and being longitudinally movable within the elongate body;
  a fluid injection tube coupled to the distal portion of the elongate body and the distal portion of the linear shaft; and
  a pliable element encompassing the fluid injection tube, the fluid injection tube being transitionable within the pliable element about the linear shaft between a linear configuration and an expanded radial configuration when the linear shaft is moved longitudinally within the elongate body, the linear shaft remaining in a linear configuration when movement of the linear shaft causes the fluid injection tube to be transitioned between the linear configuration and the expanded radial configuration,
  the fluid injection tube defining an anterior surface when the fluid injection tube is in the expanded radial configuration, the anterior surface including a plurality of apertures immediately adjacent to an inner surface of the pliable element to dispense fluid onto the inner surface of the pliable element.

2. The medical device according to claim 1, further comprising a cryogenic coolant source in fluid communication with the fluid injection tube.

3. The medical device according to claim 1, wherein the linear shaft is slidably disposed within a portion of the elongate body.

4. The medical device according to claim 3, wherein the linear shaft defines a lumen therein for passage of a guide wire.

5. The medical device according to claim 3, wherein the linear shaft is rotatable with respect to the elongate body, and wherein rotation of the linear shaft transitions the fluid injection tube between the linear configuration and the expanded radial configuration.

6. The medical device according to claim 1, wherein the fluid injection tube is constructed from a shape memory material.

7. The medical device according to claim 1, wherein the elongate body defines an exhaust lumen in fluid communication with an interior of the pliable element.

8. The medical device according to claim 1, wherein deploying the fluid injection tube into the expanded radial configuration deforms the pliable element to an expanded configuration.

9. A medical system, comprising:
  a catheter body having a longitudinal axis, a proximal portion, and a distal portion;
  a linear shaft disposed within a portion of the catheter body, the linear shaft defining a distal tip and being slidably moveable with respect to the catheter body;
  a fluid injection tube coupled to the distal portion of the catheter body and the distal tip of the linear shaft, the fluid injection tube being transitionable about the linear shaft between a first geometric configuration and a second geometric configuration when the linear shaft is slidably moved within the catheter body, the linear shaft remaining in a linear configuration when the fluid injection tube is transitioned between the first geometric configuration and the second geometric configuration by the slidably movement of the linear shaft within the catheter body;
  a membrane coupled to the shaft and enclosing at least a portion of the fluid injection tube therein; and
  a coolant source in fluid communication with the fluid injection tube,
  the fluid injection tube defining an anterior surface that lies in a plane that is substantially orthogonal to the longitudinal axis when the fluid injection tube is in the second geometric configuration, the anterior surface including a plurality of apertures immediately adjacent to an inner surface of the membrane.

10. The medical system according to claim 9, wherein the first geometric configuration is linear and the second geometric configuration is helical.

11. The medical system according to claim 10, wherein the membrane is tensioned across at least a portion of the fluid injection tube in the second geometric configuration.

12. The medical system according to claim 9, wherein the shaft defines a guide wire lumen therein.

13. A method of thermally treating tissue, comprising:
  positioning a deformable membrane adjacent to the tissue;
  transitioning a fluid injection tube within the deformable membrane about a linear shaft within the deformable membrane from a first geometric configuration to a second geometric configuration to expand the deformable membrane by retracting the linear shaft within, the linear shaft remaining in a linear configuration when the fluid injection tube transitions between the first and second geometric configurations, the fluid injection tube defining an anterior surface when the fluid injection tube is in the second geometric configuration, the anterior surface including a plurality of apertures immediately adjacent to an inner surface of the deformable membrane;
  dispersing a coolant through the fluid injection tube onto the inner surface of the deformable membrane; and
  thermally treating the tissue with the deformable membrane.

14. The method according to claim 13, wherein thermally treating the tissue includes ablating at least a portion of the tissue.

15. The method according to claim 13, wherein the tissue includes cardiac tissue.

16. The method according to claim 13, wherein the tissue includes an ostium of a pulmonary vein.

17. The method according to claim 13, wherein the first geometric configuration is linear and the second geometric configuration is helical.

18. The method according to claim 13, further comprising:
terminating coolant dispersion into the interior cavity;
transitioning the fluid injection tube from the second geometric configuration to the first configuration; and
removing the deformable membrane from the tissue.

* * * * *